(12) United States Patent
Sato et al.

(10) Patent No.: US 10,618,860 B2
(45) Date of Patent: Apr. 14, 2020

(54) HOMOALLYL HALIDE COMPOSITION AND METHOD FOR STORING HOMOALLYL HALIDE

(71) Applicant: KURARAY CO., LTD., Kurashiki-shi (JP)

(72) Inventors: Junko Sato, Tainai (JP); Katsuji Ujita, Tainai (JP); Takuo Tsuruta, Tainai (JP); Takashi Sugioka, Chiyoda-ku (JP)

(73) Assignee: KURARAY CO., LTD, Kurashiki-shi (JP)

( * ) Notice: Subject to any disclaimer, the term of this patent is extended or adjusted under 35 U.S.C. 154(b) by 99 days.

(21) Appl. No.: 15/760,405

(22) PCT Filed: Sep. 13, 2016

(86) PCT No.: PCT/JP2016/076999
§ 371 (c)(1),
(2) Date: Mar. 15, 2018

(87) PCT Pub. No.: WO2017/047591
PCT Pub. Date: Mar. 23, 2017

(65) Prior Publication Data
US 2018/0244593 A1 Aug. 30, 2018

(30) Foreign Application Priority Data
Sep. 18, 2015 (JP) ................. 2015-184595

(51) Int. Cl.
| C07C 17/42 | (2006.01) |
|---|---|
| C07C 17/16 | (2006.01) |
| C07C 21/04 | (2006.01) |
| C08F 14/04 | (2006.01) |
| C08F 14/14 | (2006.01) |

(52) U.S. Cl.
CPC .............. *C07C 17/42* (2013.01); *C07C 17/16* (2013.01); *C07C 21/04* (2013.01); *C08F 14/04* (2013.01); *C08F 14/14* (2013.01)

(58) Field of Classification Search
CPC ......... C07C 17/02; C07C 17/04; C07C 17/08; C07C 17/087; C07C 21/04; C07C 17/42; C07C 17/16; C08F 14/04; C08F 14/14
USPC ........................................................ 526/181
See application file for complete search history.

(56) References Cited

FOREIGN PATENT DOCUMENTS

| DE | 1900467 | * | 11/1969 | ........... C07C 17/281 |
|---|---|---|---|---|
| GB | 1 285 436 | A | 8/1972 | |
| JP | 46-6610 | B1 | 2/1971 | |
| JP | 47-13491 | B1 | 4/1972 | |
| JP | 53-137902 | A | 12/1978 | |
| JP | 59-65046 | A | 4/1984 | |
| JP | 3-118340 | A | 5/1991 | |
| JP | 03118340 | * | 5/1991 | ............. C07C 21/04 |
| JP | 11-130705 | A | 5/1999 | |
| JP | 2002-508405 | A | 3/2002 | |

OTHER PUBLICATIONS

International Search Report dated Dec. 13, 2016 in PCT/JP2016/076999 filed Sep. 13, 2016.
Extended European Search Report dated Apr. 15, 2019 in Patent Application No. 16846462.6, 11 pages.
Mattay, J. et al. "Photoreactions of Enones with Amines—Cyclization of Unsaturated Enones and Reductive Ring Opening by Photoinduced Electron Transfer (PET)[1]" Chemische Berichte, https://doi.org/10.1002/cber.19921250921, vol. 125, No. 9, XP055577681, 1992, pp. 2119-2127.
Sanguinetti, M. et al. "Novel Macrocyclic Amidinoureas: Potent Non-Azole Antifungals Active against Wild-Type and Resistant Candida Species" ACS Medicinal Chemistry Letters, vol. 4, No. 9, XP055131069, 2013, pp. 852-857.
Kubota, K. et al. "Synthesis and structure-activity relationship of tricyclic carboxylic acids as novel anti-histamines" Bioorganic & Medicinal Chemistry, vol. 19, No. 9, XP055150250, 2011, pp. 3005-3021.
Sarkar, S.M. et al. "Organocatalytic asymmetric synthesis of quinine and quinidine" Tetrahedron Letters, vol. 52, No. 8, XP055577663, pp. 923-927.
McBrien, H.L. et al. "Male-Produced Sex Attractant Pheromone of the Green Stink Bug, *Acrosternum hilare* (Say)" Journal of Chemical Ecology, https://link.springer.com/content/pdf/10.1023/A:1010460709535.pdf, vol. 27, No. 9, XP055577629, 2001, 19 pages.

* cited by examiner

*Primary Examiner* — Ling Siu Choi
*Assistant Examiner* — Ronald Grinsted
(74) *Attorney, Agent, or Firm* — Oblon, McClelland, Maier & Neustadt, L.L.P.

(57) ABSTRACT

There is provided a composition containing one or more basic compounds selected from the group consisting of tertiary amines, nitrogen-containing heterocyclic aromatic compounds, alkali metal carbonate salts, alkaline earth metal carbonate salts and alkali metal hydrogencarbonate salts, and a homoallyl halide.

15 Claims, No Drawings

US 10,618,860 B2

HOMOALLYL HALIDE COMPOSITION AND METHOD FOR STORING HOMOALLYL HALIDE

TECHNICAL FIELD

The present invention relates to a homoallyl halide composition, particularly to a composition containing a specific basic compound and a homoallyl halide.

BACKGROUND ART

Homoallyl halides such as 3-methyl-3-butenyl chloride are useful as raw materials for compounds or resins for medicines, silane coupling agents and the like.

Hydrocarbon halides are generally likely to decompose when exposed to heat, light, water or the like. Particularly in the case of homoallyl halides, in addition to further decomposition and isomerization by a hydrogen halide generated by the decomposition, there is a possibility of rapidly causing polymerization of conjugated dienes generated by the decomposition, which is remarkably dangerous.

Hence, homoallyl halides produced are typically quickly used for a succeeding process as they are crude products without being isolated and purified, or are handled as dilute solutions.

As means to stabilize a hydrocarbon halide, for example, Patent Literature 1 discloses a method involving using a stabilizer composition containing an N-alkylmorpholine and a straight-chain or cyclic aliphatic amine having a boiling point of at lowest 150° C. and containing no heteroatom other than N.

CITATION LIST

Patent Literature

PTL1: JP 2002-508405 A

SUMMARY OF INVENTION

Technical Problem

The method of Patent Literature 1, however, is not suitable as a method of stably storing the homoallyl halide over a long period since two kinds of basic substances are added and besides, a primary amine reactive with a homoallyl halide is also contained.

An object of the present invention is to provide a homoallyl halide composition capable of being safely and stably stored over a long period, and a method for storing the homoallyl halide composition.

Solution to Problem

As a result of exhaustive studies, the present inventors have found that the addition of a specific basic compound to a homoallyl halide suppresses generation of a hydrogen halide due to the decomposition, and even in the case where the hydrogen halide is generated, traps the hydrogen halide and can prevent rush and chain decomposition; and this finding has led to the completion of the present invention.

That is, the present invention provides the following [1] to [3].

[1] A composition containing: one or more basic compounds selected from the group consisting of tertiary amines, nitrogen-containing heterocyclic aromatic compounds, alkali metal carbonate salts, alkaline earth metal carbonate salts and alkali metal hydrogencarbonate salts; and a homoallyl halide.

[2] A composition containing: one or more basic compounds selected from the group consisting of alkali metal carbonate salts and alkaline earth metal carbonate salts; and a homoallyl halide.

[3] A method for storing a homoallyl halide, containing allowing one or more basic compounds selected from the group consisting of tertiary amines, nitrogen-containing heterocyclic aromatic compounds, alkali metal carbonate salts, alkaline earth metal carbonate salts and alkali metal hydrogencarbonate salts, to coexist with the homoallyl halide.

[4] A method for producing a compound or a resin, the method containing using a composition according to [1] or [2] as a raw material.

Advantageous Effect of Invention

The homoallyl halide composition of the present invention can be safely and stably stored over a long period, and is useful as raw material for medicines, agrochemicals, various types of chemical products, resins, silane coupling agents and the like.

DESCRIPTION OF EMBODIMENT

A "homoallyl halide" in the present invention is a general term of a compound having a carbon-carbon double bond and having a halogen atom bonded to the homoallyl position.

The halogen atom includes a fluorine atom, a chlorine atom, a bromine atom and an iodine atom. From the viewpoint of easy availability, the composition of the present invention is useful in the case where the halogen atom is a chlorine atom, that is, in the case where a homoallyl halide is a homoallyl chloride.

The homoallyl halide contained in the composition of the present invention is not especially limited. Examples of the homoallyl halide include 3-butenyl chloride, 3-methyl-3-butenyl chloride, 2-methyl-3-butenyl chloride, 4-methyl-3-pentenyl chloride, 3-hexenyl chloride, 2-isopropenyl-5-methyl-4-hexenyl chloride, 3-butenyl bromide, 3-methyl-3-butenyl bromide, 2-methyl-3-butenyl bromide, 4-methyl-3-pentenyl bromide, 3-hexenyl bromide, 2-isopropenyl-5-methyl-4hexenyl bromide, 3-butenyl iodide, 3-methyl-3-butenyl iodide, 2-methyl-3-butenyl iodide, 4-methyl-3-pentenyl iodide, 3-hexenyl iodide, 2-isopropenyl-5-methyl-4-hexenyl iodide, 3-butenyl fluoride, 3-methyl-3-butenyl fluoride, 2-methyl-3-butenyl fluoride, 4-methyl-3-pentenyl fluoride, 3-hexenyl fluoride and 2-isopropenyl-5-methyl-4-hexenyl fluoride. From the viewpoint of easy availability and usefulness, preferable is 3-butenyl chloride, 3-methyl-3-butenyl chloride, 2-methyl-3-butenyl chloride, 4-methyl-3-pentenyl chloride, 3-hexenyl chloride or 2-isopropenyl-5-methyl-4-hexenyl chloride, and more preferable is 3-butenyl chloride or 3-methyl-3-butenyl chloride.

In the present invention, commercially available homoallyl halides and those synthesized according to well-known methods can be suitably used as the homoallyl halides. For example, 3-methyl-3-butenyl chloride can be produced from 3-methyl-3-buten-1-ol according to Synthesis Example described later.

The basic compound contained in the composition of the present invention is selected from the group consisting of tertiary amines, nitrogen-containing heterocyclic aromatic compounds, alkali metal carbonate salts, alkaline earth metal carbonate salts and alkali metal hydrogencarbonate salts.

The basic compounds in the present invention do not include ammonia, primary amines, secondary amines or alkoxides. This is because these compounds may react with homoallyl halides during storage and the homoallyl halides may be consumed. These can be allowed to coexist only in the range of not inhibiting the working effect of the present invention.

The tertiary amines include triethylamine, tributylamine, trioctylamine, diisopropylethylamine and 1,4-diazabicyclo[2.2.2]octane.

The nitrogen-containing heterocyclic aromatic compounds include pyridine, 2-picoline and 2,6-lutidine.

The alkali metal carbonate salts include sodium carbonate and potassium carbonate.

The alkaline earth metal carbonate salts include magnesium carbonate and calcium carbonate.

The alkali metal hydrogencarbonate salts include sodium hydrogencarbonate and potassium hydrogencarbonate.

Among the above, preferable are tertiary amines, alkali metal carbonate salts and alkaline earth metal carbonate salts; more preferable are alkali metal carbonate salts and alkaline earth metal carbonate salts; still more preferable are alkali metal carbonate salts; and most preferable is sodium carbonate.

The amount of the basic compound to be added is not especially limited, but is preferably 0.00001 to 0.3 mass time that of the homoallyl halide; more preferably 0.0001 to 0.2 mass time; still more preferably 0.001 to 0.1 mass time; and most preferably 0.005 to 0.1 mass time.

The composition of the present invention may comprise an organic solvent in the range of not inhibiting the advantage of the present invention. Examples of the organic solvent include aliphatic hydrocarbons such as pentane, hexane, heptane and octane; aromatic hydrocarbons such as benzene, toluene, xylene and mesitylene; aromatic hydrocarbon halides such as chlorobenzene and fluorobenzene; ethers such as diethyl ether, diisopropyl ether, dibutyl ether, tetrahydrofuran, dioxane, 1,2-dimethoxyethane, Diglyme, Triglyme and Tetraglyme; and aliphatic hydrocarbon halides such as dichloromethane, chloroform and 1,2-dichloroethane. These solvents may be used singly or concurrently in two or more. The content of the solvent is not especially limited, but is preferably in the range of 0.1 to 50 mass times that of the homoallyl halide; more preferably in the range of 0.5 to 20 mass times; and still more preferably in the range of 1 to 10 mass times.

EXAMPLES

Hereinafter, the present invention will be described specifically by way of Examples, but the present invention is not limited to these Examples.

Synthesis Example 43.06 g (0.50 mol) of 3-methyl-3-buten-1-ol, 55.65 g (0.55 mol) of triethylamine and 200 g of ether were charged in a 500-ml reactor equipped with a stirrer, a cooling tube, a thermometer and a dropping funnel, and the interior mixture was cooled down to 5° C. under stirring. Then, 65.43 g (0.55 mol) of thionyl chloride was dropwise charged over 2.5 hours while the internal temperature was held at 10° C. or lower. After the dropping, the resultant mixture was heated up to an internal temperature of 50 to 55° C., and heated and stirred for 13 hours. After cooling, 125 g of water was added, stirred and allowed to stand; thereafter, a water phase was separated, and further an organic phase was washed with 130 g of a 5% sodium hydrogencarbonate aqueous solution and 125 g of water. The separated organic phase was obtained in 235.2 g, and analyzed by gas chromatography; as a result of the analysis, the organic phase contained 46.5 g (0.44 mol, yield: 88%) of 3-methyl-3-butenyl chloride. The reaction solution was distilled under reduced pressure to thereby obtain 23.3 g (distillation yield: 50%) of 3-methyl-3-butenyl chloride (hereinafter, designated as IPEC) of 99% or higher in purity.

Examples, Comparative Examples and Reference Examples

Each composition indicated in Table 1 was analyzed for the remaining ratio at every predetermined time of each hydrocarbon halide under stirring by gas chromatography.

Here, in the present Examples, trimethylamine ($NEt_3$) was present in the state of being completely dissolved in IPEC, and sodium carbonate ($Na_2CO_3$) was present in the state of being suspended in IPEC. The each composition was allowed to coexist with, in addition to the substances in the Table, 5 parts by mass of decane as an internal standard substance, and the remaining ratio was calculated by measuring changes in the proportion of the hydrocarbon halide to the internal standard substance.

TABLE 1

| | Composition | | | Elapsed time and remaining ratio (%) | | |
|---|---|---|---|---|---|---|
| | Hydrocarbon halide | Basic compound | Temperature (° C.) | 0 hour | 13 hours | 24 hours |
| Example 1 | 3-methyl-3-butenyl chloride 100 parts by mass | $Na_2CO_3$ | 5 parts by mass | 80 | 100 | 98 | 96 |
| Example 2 | | $Na_2CO_3$ | 5 parts by mass | 50 | 100 | 100 | 100 |
| Example 3 | | $NEt_3$ | 5 parts by mass | 80 | 100 | 84 | 73 |
| Comparative Example 1 | | — | — | 80 | 100 | 67 | 53 |
| Comparative Example 2 | | — | — | 50 | 100 | 95 | 87 |

TABLE 1-continued

| | Composition | | Temperature | Elapsed time and remaining ratio (%) | | |
|---|---|---|---|---|---|---|
| | Hydrocarbon halide | Basic compound | (° C.) | 0 hour | 13 hours | 24 hours |
| Reference Example 1 | allyl chloride | — | 45 (reflux) | 100 | 100 | 100 |
| Reference Example 2 | 7-octenyl chloride | — | 80 | 100 | 100 | 100 |

From the results of the Examples and the Comparative Examples, it was found that the composition of the present invention was able to be stored safely and stably even in a high-temperature state. Further from the results of the Reference Examples, it was implied that the decrease in the remaining ratio during storage was a problem characteristic of the homoallyl halide.

INDUSTRIAL APPLICABILITY

The homoallyl halide composition of the present invention can be safely and stably stored over a long period, and is useful as a raw material for medicines, agrochemicals, various types of chemical products, resins, silane coupling agents and the like.

The invention claimed is:

1. A composition, comprising:
   at least one basic compound selected from the group consisting of a tertiary amine, a nitrogen-containing heterocyclic aromatic compound, an alkali metal carbonate salt, an alkaline earth metal carbonate salt and an alkali metal hydrogencarbonate salt; and
   a homoallyl halide.

2. A composition, comprising:
   at least one basic compound selected from the group consisting of an alkali metal carbonate salt and an alkaline earth metal carbonate salt; and
   a homoallyl halide.

3. A method for storing a homoallyl halide, the method comprising allowing at least one basic compound selected from the group consisting of a tertiary amine, a nitrogen-containing heterocyclic aromatic compound, an alkali metal carbonate salt, an alkaline earth metal carbonate salt and an alkali metal hydrogencarbonate salt, to coexist with the homoallyl halide.

4. A method for producing a compound or a resin, the method comprising using the composition according to claim 1 as a raw material.

5. A method for producing a compound or a resin, the method comprising using the composition according to claim 2 as a raw material.

6. The composition of claim 1, wherein a mass ratio of the at least one basic compound to the homoallyl halide is from 0.00001:1 to 0.3:1.

7. The composition of claim 1, further comprising an organic solvent.

8. The composition of claim 2, wherein a mass ratio of the at least one basic compound to the homoallyl halide is from 0.00001:1 to 0.3:1.

9. The composition of claim 2, further comprising an organic solvent.

10. The composition of claim 7, wherein the organic solvent is at least one selected from the group consisting of an aliphatic hydrocarbon, aromatic hydrocarbon, ether, and an aliphatic hydrocarbon halide.

11. The composition of claim 8, wherein the organic solvent is at least one selected from the group consisting of an aliphatic hydrocarbon, aromatic hydrocarbon, ether, and an aliphatic hydrocarbon halide.

12. The composition of claim 7, wherein a mass ratio of the organic solvent to the homoallyl halide is form the 0.1:1 to 50:1.

13. The composition of claim 8, wherein a mass ratio of the organic solvent to the homoallyl halide is form the 0.1:1 to 50:1.

14. The composition of claim 1, wherein the homoallyl halide is at least one selected from the group consisting of 3-butenyl chloride, 3-methyl-3-butenyl chloride, 2-methyl-3-butenyl chloride, 4-methyl-3-pentenyl chloride, 3-hexenyl chloride, 2-isopropenyl-5-methyl-4-hexenyl chloride, 3-butenyl bromide, 3-methyl-3-butenyl bromide, 2-methyl-3-butenyl bromide, 4-methyl-3-pentenyl bromide, 3-hexenyl bromide, 2-isopropenyl-5-methyl-4-hexenyl bromide, 3-butenyl iodide, 3-methyl-3-butenyl iodide, 2-methyl-3-butenyl iodide, 4-methyl-3-pentenyl iodide, 3-hexenyl iodide, 2-isopropenyl-5-methyl-4-hexenyl iodide, 3-butenyl fluoride, 3-methyl-3-butenyl fluoride, 2-methyl-3-butenyl fluoride, 4-methyl-3-pentenyl fluoride, 3-hexenyl fluoride, and 2-isopropenyl-5-methyl-4-hexenyl fluoride.

15. The composition of claim 2, wherein the homoallyl halide is at least one selected from the group consisting of 3-butenyl chloride, 3-methyl-3-butenyl chloride, 2-methyl-3-butenyl chloride, 4-methyl-3-pentenyl chloride, 3-hexenyl chloride, 2-isopropenyl-5-methyl-4-hexenyl chloride, 3-butenyl bromide, 3-methyl-3-butenyl bromide, 2-methyl-3-butenyl bromide, 4-methyl-3-pentenyl bromide, 3-hexenyl bromide, 2-isopropenyl-5-methyl-4-hexenyl bromide, 3-butenyl iodide, 3-methyl-3-butenyl iodide, 2-methyl-3-butenyl iodide, 4-methyl-3-pentenyl iodide, 3-hexenyl iodide, 2-isopropenyl-5-methyl-4-hexenyl iodide, 3-butenyl fluoride, 3-methyl-3-butenyl fluoride, 2-methyl-3-butenyl fluoride, 4-methyl-3-pentenyl fluoride, 3-hexenyl fluoride, and 2-isopropenyl-5-methyl-4-hexenyl fluoride.

\* \* \* \* \*